United States Patent
Aoyagi et al.

(10) Patent No.: US 8,306,606 B2
(45) Date of Patent: Nov. 6, 2012

(54) MEDICAL IMAGING APPARATUS, ULTRASONIC IMAGING APPARATUS, MAGNETIC RESONANCE IMAGING APPARATUS, MEDICAL IMAGE PROCESSING APPARATUS, AND MEDICAL IMAGE PROCESSING METHOD

(75) Inventors: Kota Aoyagi, Yaita (JP); Hitoshi Yamagata, Otawara (JP); Takehiro Ema, Otawara (JP); Kyoko Sato, Nasushiobara (JP); Shunsuke Satoh, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 671 days.

(21) Appl. No.: 12/363,060

(22) Filed: Jan. 30, 2009

(65) Prior Publication Data
US 2009/0198123 A1 Aug. 6, 2009

(30) Foreign Application Priority Data
Feb. 4, 2008 (JP) ................................ 2008-024296

(51) Int. Cl.
*A61B 6/00* (2006.01)
(52) U.S. Cl. ........ 600/431; 600/407; 600/437; 600/454; 600/465; 600/468
(58) Field of Classification Search .................. 600/407, 600/437, 410, 425, 458, 454, 449; 382/128
See application file for complete search history.

(56) References Cited

U.S. PATENT DOCUMENTS

| 6,283,918 B1 * | 9/2001 | Kanda et al. | 600/441 |
| 6,480,732 B1 * | 11/2002 | Tanaka et al. | 600/425 |
| 2007/0238960 A1 * | 10/2007 | Thorn | 600/407 |

FOREIGN PATENT DOCUMENTS
JP 11-164833 6/1999
(Continued)

OTHER PUBLICATIONS

Masatoshi Kudo, et al., "A Proposal of Novel Treatment-assist Technique for Hepatocellular Carcinoma in the Sonazoid-enhanced Ultrasonography: Value of Defect Re-Perfusion Imaging", Kanzo, vol. 48, No. 6, 2007, pp. 299-301 (with English Abstract).

(Continued)

*Primary Examiner* — Tse Chen
*Assistant Examiner* — Joel F Brutus
(74) *Attorney, Agent, or Firm* — Oblon, Spivak, McClelland, Maier & Neustadt, L.L.P.

(57) ABSTRACT

A differential-image creating unit creates a three-dimensional image on which an artery is highlighted and a three-dimensional image on which a tumor is highlighted. An image compositing unit combines the three-dimensional images to composite an image. A display control unit displays the composite image on a monitor. Moreover, when compositing an image, the image compositing unit composites the image such that a tumor nutrient blood-flow inside and outside tumor is to be displayed in respective different colors. Furthermore, a blood-flow quantity inside tumor measuring unit calculates a blood-flow quantity inside tumor and a ratio of the blood-flow quantity inside tumor to a tumor volume, and the display control unit displays the blood-flow quantity inside tumor and the ratio of the blood-flow quantity inside tumor to the tumor volume. Accordingly, information that is meaningful for determining malignancy of a tumor can be provided.

6 Claims, 5 Drawing Sheets

FOREIGN PATENT DOCUMENTS

| | | |
|---|---|---|
| JP | 2004-147823 | 5/2004 |
| JP | 2004-315424 | 5/2004 |
| JP | 2005-006718 | 1/2005 |
| JP | 2006-122643 | 5/2006 |
| JP | 2007-125169 | 5/2007 |
| JP | 2007-301005 | 11/2007 |
| JP | 2008-80158 | 4/2008 |

OTHER PUBLICATIONS

Office Action (with English translation) mailed on Jul. 31, 2012, in counterpart Japanese Patent Appln. No. 2008-024296 (6 pages).

* cited by examiner

FIG.7

MEDICAL IMAGING APPARATUS, ULTRASONIC IMAGING APPARATUS, MAGNETIC RESONANCE IMAGING APPARATUS, MEDICAL IMAGE PROCESSING APPARATUS, AND MEDICAL IMAGE PROCESSING METHOD

CROSS-REFERENCE TO RELATED APPLICATIONS

This application is based upon and claims the benefit of priority from the prior Japanese Patent Application No. 2008-024296, filed on Feb. 4, 2008; the entire contents of which are incorporated herein by reference.

BACKGROUND OF THE INVENTION

1. Field of the Invention

The present invention relates to a displaying technology of a tumor nutrient blood-flow in imaging of a tumor performed by using a contrast medium.

2. Description of the Related Art

Recently, a microbubble ultrasonic contrast medium for intravenous injection of which microbubbles enhance echo reflection has been commercially manufactured, and a contrast echo method has been performed. According to this method, a blood-flow signal can be enhanced with microbubbles introduced in a blood vessel, and blood-flow dynamic states can be clearly observed. Moreover, microbubbles have a characteristic that they are specifically englobed by Kupffer cells in a liver, thereby being expected to be effective in a field of hepatic tumor diagnosis.

According to the contrast echo method, observed images largely vary depending on a time phase for imaging. In other words, in an artery phase that appears after over ten seconds from an intravenous injection, an image with an enhanced artery blood flow is obtained. On the other hand, in a late phase that appears after a few minutes from the intravenous injection, hepatic parenchyma is enhanced as microbubbles are captured in Kupffer cells, consequently, a tumor in which Kupffer cells decrease to fewer than those in normal tissues gives a low signal, so that an image on which a tumor form is recognized can be obtained.

Recently, a contrast medium called a next-generation contrast medium has appeared with which long-time imaging can be achieved at a low sound pressure. One of the next-generation contrast mediums was approved in December 2006 in Japan, and its clinical application has been progressing.

Regarding the contrast echo method, developments are made in a technology of displaying an elapse time from an injection of a contrast medium into a subject, and a technology of additionally displaying the number of doses for indicating which dose of the contrast medium an elapse time corresponds to (for example, see JP-A 2007-301005 (KOKAI)).

To diagnose a tumor, presence and dynamic states of an artery that provides nutrition to the tumor are important, so that image diagnosis needs to be performed by combining an image in the artery phase and an image in the late phase. However, any method that can display such combination effectively has not been provided.

SUMMARY OF THE INVENTION

According to one aspect of the present invention, a medical imaging apparatus includes an imaging-data collecting unit that collects imaging data by imaging a subject to whom a contrast medium is injected; a first image creating unit that creates a first image on which an artery blood flow is highlighted, based on imaging data in an artery phase from which artery blood-flow dynamic states can be observed; a second image creating unit that creates a second image on which a tumor is highlighted, based on imaging data in a late phase from which presence of a tumor can be determined; an image compositing unit that creates a third image by combining the first image and the second image; and an image display unit that displays the third image composited by the image compositing unit.

According to another aspect of the present invention, an ultrasonic imaging apparatus includes an imaging-data collecting unit that collects imaging data by imaging a subject to whom a contrast medium is injected; a first image creating unit that creates a first image on which an artery blood flow is highlighted, based on imaging data in an artery phase from which artery blood-flow dynamic states can be observed; a second image creating unit that creates a second image on which a tumor is highlighted, based on imaging data in a late phase from which presence of a tumor can be determined; an image compositing unit that creates a third image by combining the first image and the second image; and an image display unit that displays the third image composited by the image compositing unit.

According to still another aspect of the present invention, a magnetic resonance imaging apparatus includes an imaging-data collecting unit that collects imaging data by imaging a subject to whom a contrast medium is injected; a first image creating unit that creates a first image on which an artery blood flow is highlighted, based on imaging data in an artery phase from which artery blood-flow dynamic states can be observed; a second image creating unit that creates a second image on which a tumor is highlighted, based on imaging data in a late phase from which presence of a tumor can be determined; an image compositing unit that creates a third image by combining the first image and the second image; and an image display unit that displays the third image composited by the image compositing unit.

According to still another aspect of the present invention, a medical image processing apparatus includes an imaging-data acquiring unit that acquires imaging data obtained by imaging a subject to whom a contrast medium is injected; a first image creating unit that creates a first image on which an artery blood flow is highlighted, based on imaging data in an artery phase from which artery blood-flow dynamic states can be observed; a second image creating unit that creates a second image on which a tumor is highlighted, based on imaging data in a late phase from which presence of a tumor can be determined; an image compositing unit that creates a third image by combining the first image and the second image; and an image display unit that displays the third image composited by the image compositing unit.

According to still another aspect of the present invention, a medical image processing method includes acquiring imaging data obtained by imaging a subject to whom a contrast medium is injected; creating a first image on which an artery blood flow is highlighted, based on imaging data in an artery phase from which artery blood-flow dynamic states can be observed; creating a second image on which a tumor is highlighted, based on imaging data in a late phase from which presence of a tumor can be determined; creating a third image by combining the first image and the second image; and displaying the composited third image.

DETAILED DESCRIPTION OF THE INVENTION

An exemplary embodiment of a medical imaging apparatus, an ultrasonic imaging apparatus, a magnetic resonance imaging apparatus, a medical image processing apparatus, and a medical image processing method will be explained below in detail with reference to the accompanying drawings.

First of all, a composite image displayed by an ultrasonic diagnostic apparatus according to an embodiment of the present invention is explained below. The ultrasonic diagnostic apparatus according to the embodiment collects three data in different time phases in contrast ultrasonic imaging, and creates and displays a composite image. FIGS. 1A to 1E are schematic diagrams for explaining a composite image displayed by the ultrasonic diagnostic apparatus according to the embodiment.

Figures 1A, 1B:
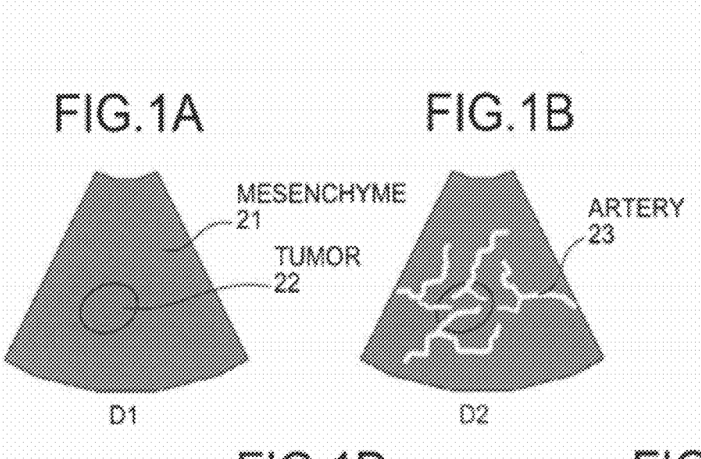
FIGS. 1A to 1E are schematic diagrams for explaining a composite image displayed by an ultrasonic diagnostic apparatus according to an embodiment of the present invention.
Figure 1C:
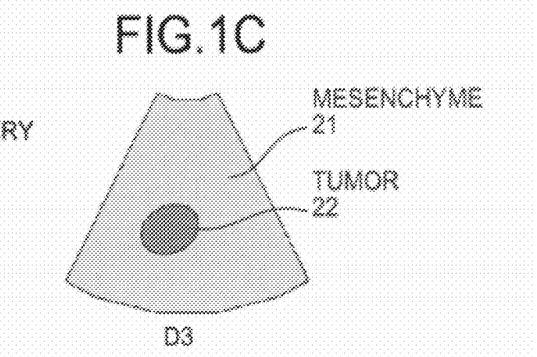

FIG. 1A depicts a B mode image D1 that is taken before a contrast medium injection or immediately after the injection; FIG. 1B depicts a B mode image D2 in an artery phase after the contrast medium injection; and FIG. 1C depicts a B mode image D3 in a late phase after the contrast medium injection.

These images have respective different characteristics. D1 is a usual B mode image, and a reference image in the embodiment. D2 is a B mode image in the artery phase, and an artery 23 gives a higher signal than that in D1. D3 is a B mode image in the late phase, and a parenchyma 21 gives a slightly high signal, and a tumor 22 gives a low signal.

Figures 1D, 1E:
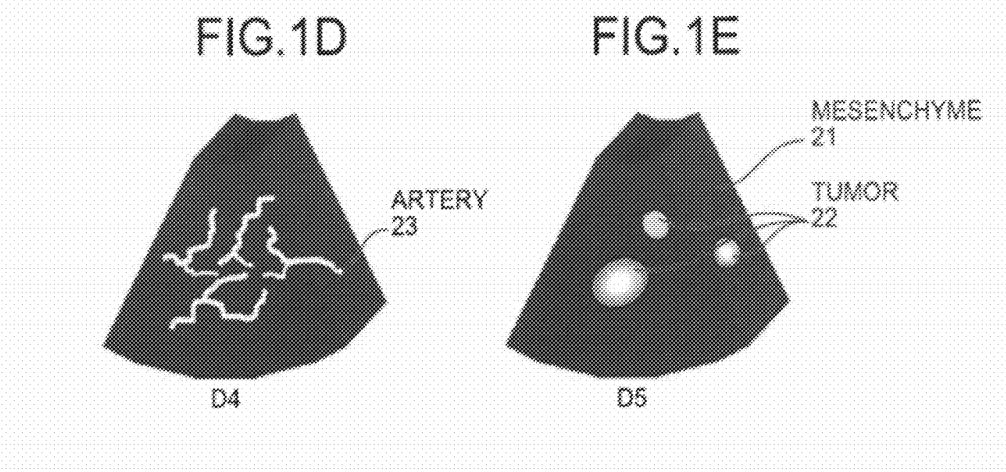

The ultrasonic diagnostic apparatus according to the embodiment creates an image D4 on which the artery 23 is highlighted based on a differential between D2 and D1. Moreover, the ultrasonic diagnostic apparatus creates an image D5 on which the tumor 22 is highlighted by inversing the brightness of D3. The ultrasonic diagnostic apparatus then displays a composite image by combining D4 and D5. When displaying the composite image, a blood flow inside tumor and a blood flow outside tumor are displayed in different colors.

In this way, the ultrasonic diagnostic apparatus according to the embodiment creates the image D4 on which the artery 23 is highlighted, and the image D5 on which the tumor 22 is highlighted, and displays a composite image by combining D4 and D5. When displaying the composite image, a blood flow inside tumor and a blood flow outside tumor are displayed in different colors. Accordingly, a tumor and blood-flow dynamic states can be simultaneously observed. Moreover, blood-flow dynamic states inside tumor can be easily observed.

Figure 2:
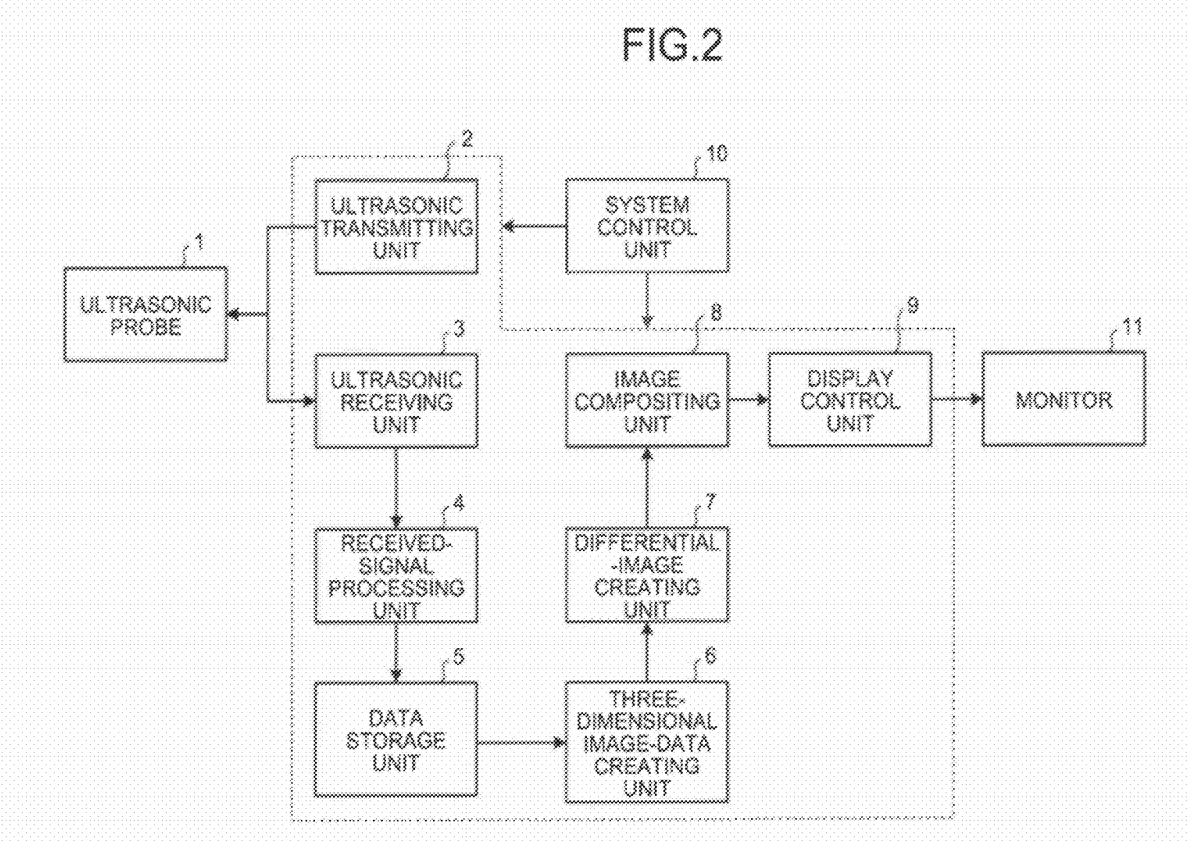
FIG. 2 is a functional block diagram of a configuration of the ultrasonic diagnostic apparatus according to the embodiment.

A configuration of the ultrasonic diagnostic apparatus according to the embodiment is explained below. FIG. 2 is a functional block diagram of a configuration of the ultrasonic diagnostic apparatus according to the embodiment. As shown in the figure, the ultrasonic diagnostic apparatus includes an ultrasonic probe 1, an ultrasonic transmitting unit 2, an ultrasonic receiving unit 3, a received-signal processing unit 4, a data storage unit 5, a three-dimensional image-data creating unit 6, a differential-image creating unit 7, an image compositing unit 8, a display control unit 9, a system control unit 10, and a monitor 11.

The ultrasonic probe 1 includes a plurality of piezoelectric vibrator elements (hereinafter, "vibrator elements") that transmits an ultrasonic pulse to a two-dimensional region or a three-dimensional region in a subject, and converts an ultrasonic reflection wave obtained from the subject into an electric signal. The ultrasonic transmitting unit 2 supplies to the vibrator elements of the ultrasonic probe 1 a driving signal for transmitting an ultrasonic pulse in a certain direction of the subject.

The ultrasonic receiving unit 3 receives signals of a plurality of channels obtained from the vibrator elements of the ultrasonic probe 1. The received-signal processing unit 4 creates B mode data by performing signal processing on signals obtained by the ultrasonic receiving unit 3, and stores the created data in the data storage unit 5. The data storage unit 5 primarily stores therein B mode data obtained by the received-signal processing unit 4.

The three-dimensional image-data creating unit 6 creates three-dimensional image data from B mode data stored in the data storage unit 5. The differential-image creating unit 7 creates a differential image by performing subtraction with respect to each voxel by using two different three-dimensional data created by the three-dimensional image-data creating unit 6. Moreover, the differential-image creating unit 7 performs processing of inversing the brightness of a three-dimensional image created by the three-dimensional image-data creating unit 6. The differential-image creating unit 7 passes the created differential image and the image of which brightness has been inversed to the image compositing unit 8 without storing them in the data storage unit 5.

The image compositing unit 8 combines a plurality of three-dimensional image data obtained by the three-dimensional image-data creating unit 6 and the differential-image creating unit 7 to composite an image. The display control unit 9 displays a composite image created by the image compositing unit 8 on the monitor 11. The system control unit 10 controls the ultrasonic diagnostic apparatus overall, and causes the ultrasonic diagnostic apparatus to operate as one apparatus.

Figure 3:
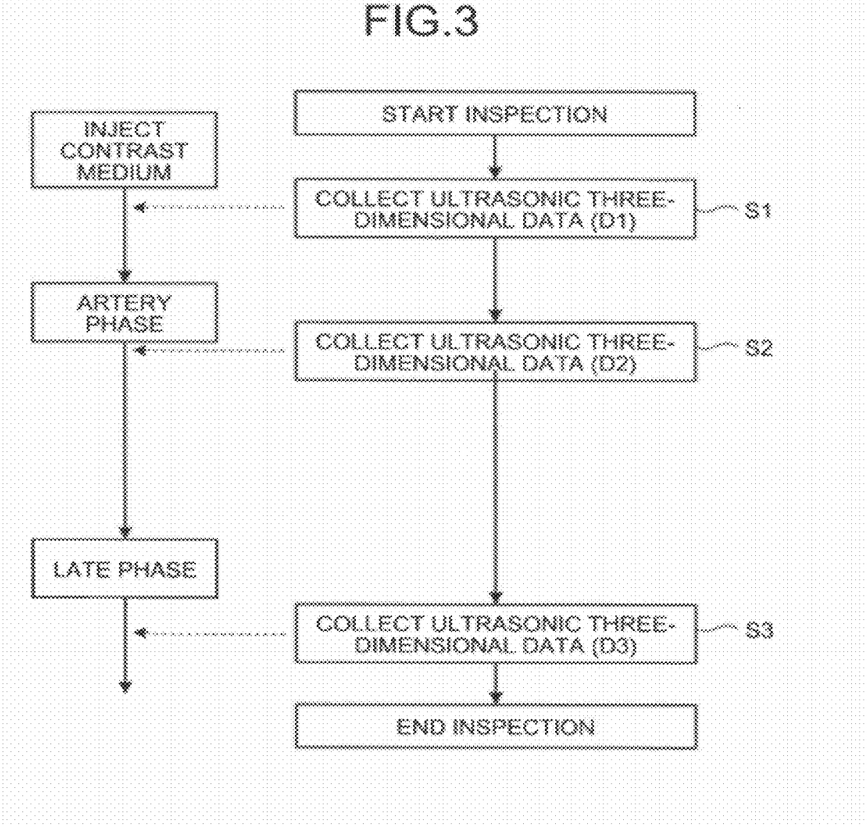
FIG. 3 is a schematic diagram for explaining data collection performed by the ultrasonic diagnostic apparatus according to the embodiment.

Data collection performed by the ultrasonic diagnostic apparatus according to the embodiment is explained below. FIG. 3 is a schematic diagram for explaining data collection performed by the ultrasonic diagnostic apparatus according to the embodiment. As shown in the figure, the ultrasonic diagnostic apparatus according to the embodiment collects three-dimensional data for D1 immediately after a contrast medium injection into the subject (Step S1). Alternatively, the data collection for D1 can be performed before the contrast medium injection.

The ultrasonic diagnostic apparatus then collects three-dimensional data for the image D2 in the artery phase (Step S2). The ultrasonic diagnostic apparatus then collects three-dimensional data for the image D3 in the late phase (Step S3). Collection timing for D1, D2, and D3 can be given by an input from a user, or can be automatically given by using collection timing that is calculated in accordance with a predetermined contrast enhancement protocol.

Figure 4:
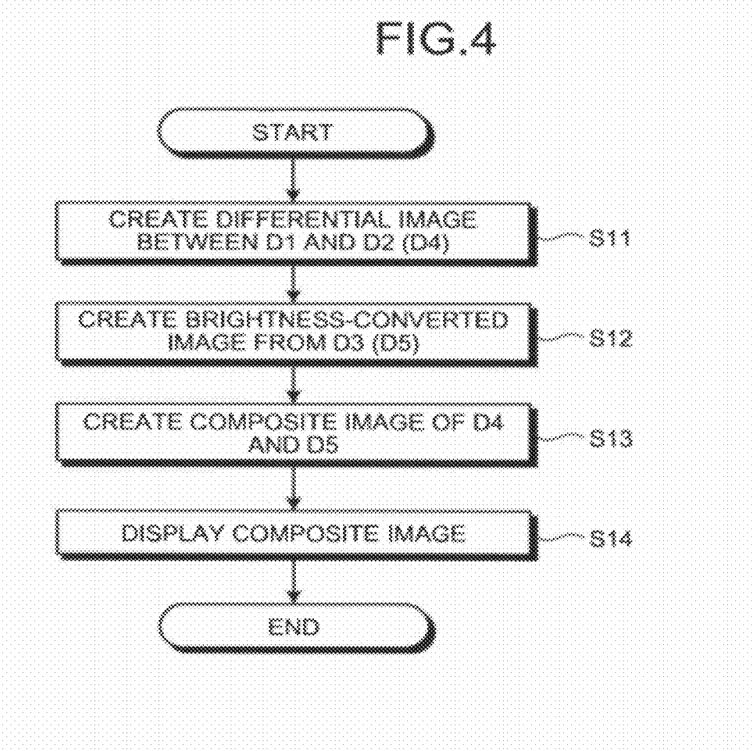
FIG. 4 is a flowchart of a procedure of composite-image display processing performed by the ultrasonic diagnostic apparatus according to the embodiment.

A procedure of composite-image display processing performed by the ultrasonic diagnostic apparatus according to the embodiment is explained below. FIG. 4 is a flowchart of a procedure of composite-image display processing performed by the ultrasonic diagnostic apparatus according to the embodiment. As shown in the figure, in the composite-image display processing, the three-dimensional image-data creating unit 6 reads data from the data storage unit 5, and creates three-dimensional images D1 and D2; and then the differential-image creating unit 7 creates a differential image D4 from D1 and D2 (Step S11).

Specifically, the differential-image creating unit 7 subtracts a voxel value assigned to each voxel of D1 from a voxel value assigned to each corresponding voxel of D2. By performing the operation, a three-dimensional image on which only an artery portion giving a high signal on D2 is highlighted can be created.

The three-dimensional image-data creating unit 6 then reads data from the data storage unit 5, and creates a three-dimensional image D3; and then the differential-image creating unit 7 performs data conversion on D3 such that low-signal part is to be highlighted and displayed (Step S12). In other words, the three-dimensional image-data creating unit 6 creates an image D5 on which display brightness is inversed. The reason for this is because a hepatic tumor that is a region of interest gives a low signal on D3, and hepatic parenchyma other than the tumor gives a slightly high signal, so that the hepatic tumor that is the region of interest is highlighted on display by performing data conversion.

Figure 5:
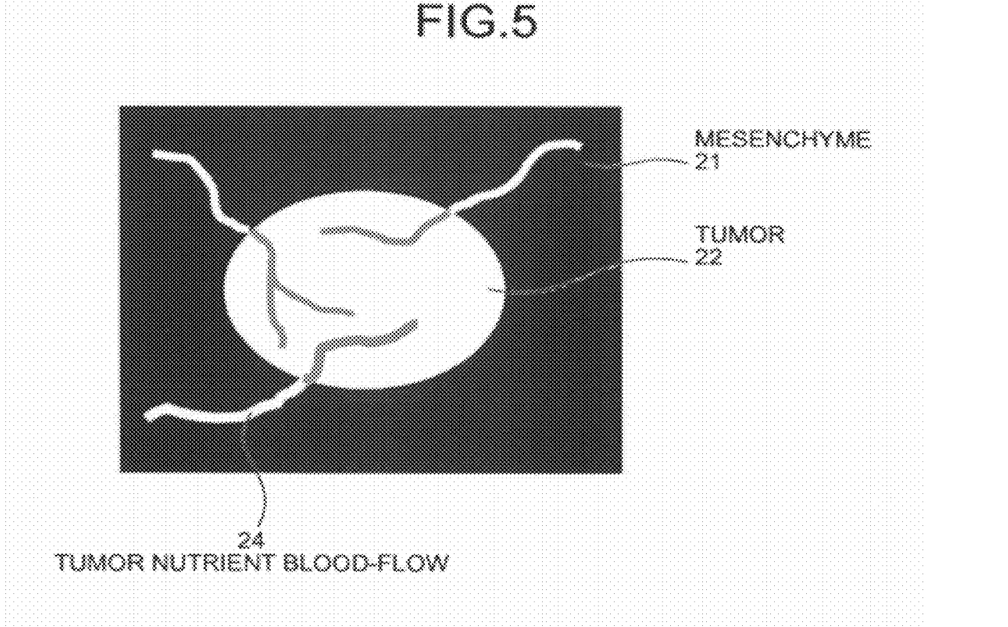
FIG. 5 is an enlarged view of a part of a composite image according to the embodiment.

The image compositing unit 8 then creates a composite image by combining D4 and D5 (Step S13), and then the display control unit 9 displays the composite image on the monitor 11 (Step S14). FIG. 5 is an enlarged view of a part of a composite image. When compositing an image, the image compositing unit 8 composites an image such that a tumor nutrient blood-flow 24 inside and outside tumor is to be displayed differently in color. Although the tumor nutrient blood-flow 24 inside and outside tumor is shown in different brightness in FIG. 5, it is to be displayed in different colors on an actual color image.

Figure 6:
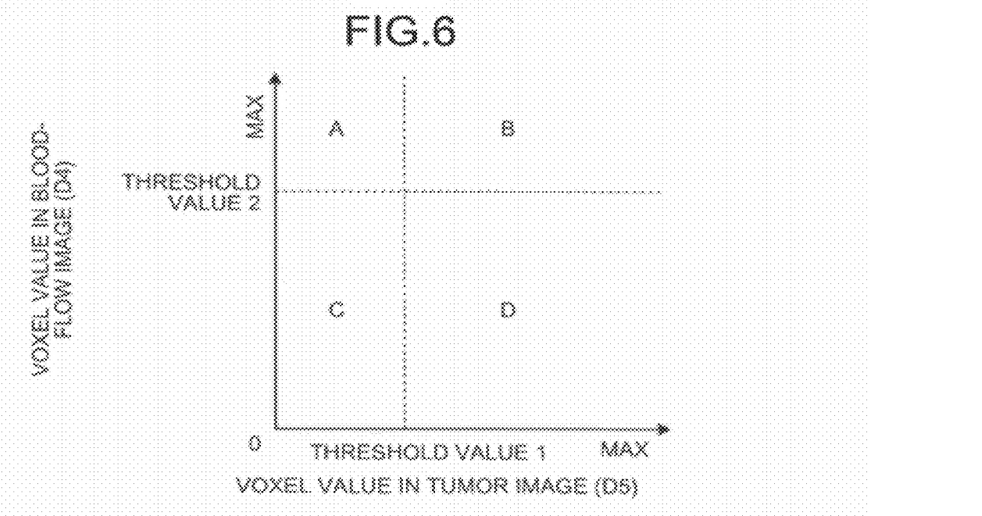
FIG. 6 is a schematic diagram for explaining a method of compositing a tumor nutrient blood-flow by an image compositing unit.

FIG. 6 is a schematic diagram for explaining a method of compositing the tumor nutrient blood-flow 24 by the image compositing unit 8. The figure is a graph on which the voxel value in D5 is arranged on the horizontal axis, and the voxel value in D4 is arranged on the vertical axis. As shown in the figure, a region indicating combinations of voxel values in D5 and voxel values in D4 is divided into four regions A to D by using a threshold value 1 and a threshold value 2. The threshold value 1 is a value that distinguishes D5, i.e., a tumor portion on a tumor image, from the other regions, and the image compositing unit 8 determines that a combination in the regions (B and D) in which voxel values are larger than the threshold value 1 corresponds to a tumor portion.

On the other hand, the threshold value 2 is a value that distinguishes D4, i.e., a blood flow portion on a blood-flow image, from the other regions, and the image compositing unit 8 determines that a combination in the regions (A and B) in which voxel values are larger than the threshold value 2 corresponds to a blood flow portion. In this way, a blood flow inside tumor is expressed as the region B.

Figure 7:
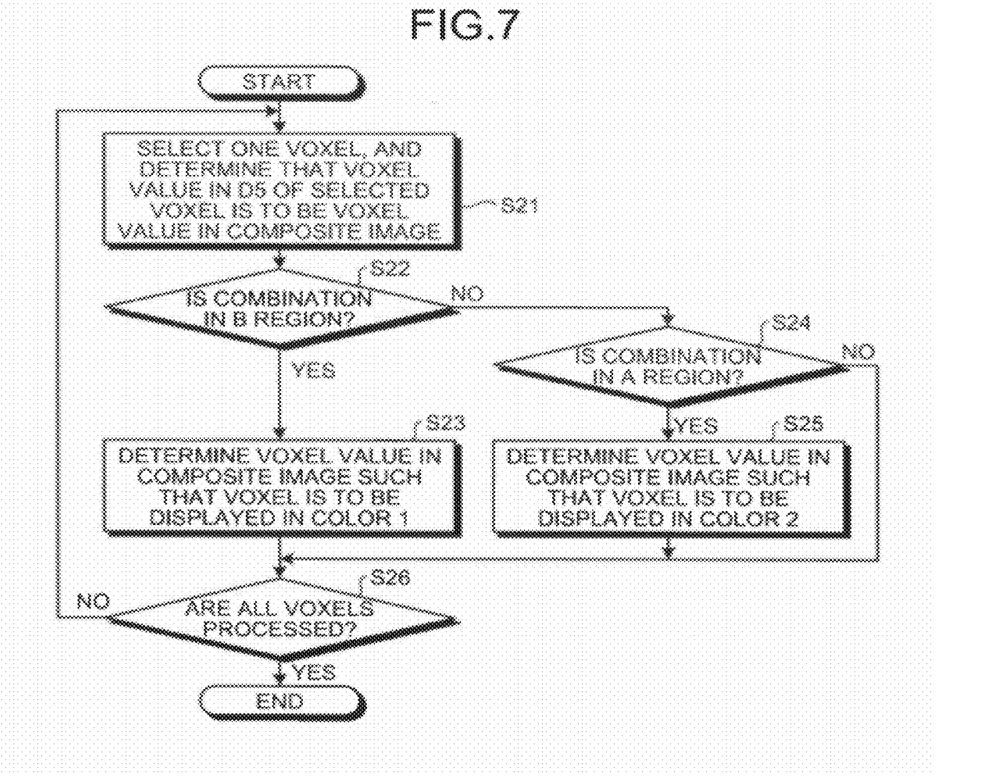
FIG. 7 is a flowchart of a procedure of image composition processing performed by the image compositing unit.

FIG. 7 is a flowchart of a procedure of image composition processing performed by the image compositing unit 8. As shown in the figure, the image compositing unit 8 selects one voxel at first, and determines that the voxel value in D5 of the selected voxel is to be a voxel value in a composite image (Step S21).

The image compositing unit 8 then finds the voxel value of a voxel at the same position on D4, and determines whether a combination of the voxel values in D4 and D5 is in the B region in FIG. 6 (Step S22). As a result, if the combination is in the B region, the image compositing unit 8 determines a voxel value in the composite image such that the voxel is to be displayed in a color 1 (Step S23); by contrast, if the combination is not in the B region, the image compositing unit 8 determines whether the combination is in the A region (Step S24).

As a result, if the combination is in the A region, the image compositing unit 8 determines the voxel value such that the voxel is to be displayed in a color 2 (Step S25). If the combination is not in the A region, that is, it is in the C or D region, in which the voxel value in D4 is small, the voxel is not particularly colored.

It is then determined whether all voxels are processed (Step S26); if there is any voxel that is not processed, the process control goes back to Step S21; or if all voxels are processed, the image composition processing is terminated. Consequently, the composite image as shown in FIG. 5 is obtained.

In this way, by compositing an image such that voxels are to be displayed differently in color depending on whether a combination of voxel values in D4 and D5 is in the B region in FIG. 6 or in the A region, the tumor nutrient blood-flow 24 inside and outside tumor can be displayed in respective different colors.

Although the image composition is performed by determining whether a voxel is inside a tumor via threshold value processing in this case; in addition to this, a tumor portion can be extracted by using the region growing method, and the display color of D4 can be changed to be different between inside and outside the extracted region.

Moreover, although the tumor nutrient blood-flow 24 inside and outside tumor is displayed in respective different colors in this case, the tumor nutrient blood-flow 24 inside and outside tumor can be displayed differently by another method, for example, by displaying the tumor nutrient blood-flow 24 in different brightness in a case of black-and-white display.

As described above, according to the embodiment, the differential-image creating unit 7 creates the three-dimensional image D4 on which the artery 23 is highlighted and the three-dimensional image D5 on which the tumor 22 is highlighted; the image compositing unit 8 combines the three-dimensional images D4 and D5 to composite an image; and the display control unit 9 displays the composite image on the monitor 11; so that a tumor and blood-flow dynamics can be simultaneously observed by using characteristics of contrast ultrasonic imaging.

Moreover, according to the embodiment, when compositing an image, the image compositing unit 8 composites the image such that the tumor nutrient blood-flow 24 inside and outside tumor is to be displayed in respective different colors, so that dynamic states of a nutrient vessel inside tumor can be easily observed, which is meaningful for determining malignancy of a tumor.

Although the embodiment is explained above in a case of using B mode data in the artery phase, the present invention is not limited to this, and can be similarly applied to a case of using Doppler data. When using Doppler data, because the Doppler data itself indicates blood-flow dynamic states, a differential image does not need to be created to highlight an artery blood flow. Timing of collecting Doppler data can be the same timing as that of collecting D3, so that data collection can be completed through one time of collection.

Furthermore, the embodiment is explained above in a case of creating and displaying a composite image of a hepatic tumor and a blood flow; however, the present invention is not limited to this, and can be similarly applied to a case of creating and displaying a composite image of another tumor and a blood flow.

Moreover, although the embodiment is explained above in a case of displaying the tumor nutrient blood-flow 24 inside and outside tumor in respective different colors; furthermore, a blood-flow quantity inside tumor can be measured and displayed. Specifically, a blood-flow quantity inside tumor measuring unit that measures a blood-flow quantity inside tumor and a ratio of the blood-flow quantity inside tumor to a tumor volume is provided in the ultrasonic diagnostic apparatus, and the display control unit 9 displays the blood-flow quantity inside tumor and the ratio of the blood-flow quantity inside tumor to the tumor volume in addition to a composite image.

The blood-flow quantity inside-tumor measuring unit counts the number of voxels of which combinations of voxel values in D4 and D5 are in the B region or the D region in FIG. 6, and calculates a blood-flow quantity inside tumor Va and a tumor volume Vt by multiplying the volume of a voxel by the number of voxels corresponding to the B region, and the number of voxels corresponding to the regions B and D, respectively. The blood-flow quantity inside-tumor measuring unit then calculates Va/Vt, a ratio of the blood-flow quantity inside tumor Va to the tumor volume Vt, and passes Va/Vt and Va to the display control unit 9. The display control unit 9 then displays Va/Vt and Va.

In this way, the blood-flow quantity inside-tumor measuring unit calculates Va/Vt and Va, and the display control unit 9 displays Va/Vt and Va, accordingly, a blood-flow quantity inside tumor and a ratio of the blood-flow quantity inside tumor to a tumor volume, which are meaningful information for determining malignancy of a tumor, can be provided.

Moreover, the embodiment is explained about an ultrasonic diagnostic apparatus; however, the present invention is not limited to this, and can be similarly applied to an ultrasonic image-processing apparatus that creates a composite image by using image data collected by an ultrasonic diagnostic apparatus, and displays the created composite image on a monitor. In other words, the present invention can be similarly applied to an ultrasonic image-processing apparatus that includes the three-dimensional image-data creating unit 6, the differential-image creating unit 7, the image compositing unit 8, the display control unit 9, the monitor 11, and a control unit that controls these units.

Moreover, the present invention can be similarly applied to an ultrasonic image-processing program that implements functions of such ultrasonic image-processing apparatus with a computer. In other words, the present invention can be similarly applied to an ultrasonic image-processing program that includes the three-dimensional image-data creating unit 6, the differential-image creating unit 7, the image compositing unit 8, the display control unit 9, and a control unit that controls these units.

Furthermore, the embodiment is explained above in a case where image data are collected by using an ultrasonic diagnostic apparatus; however, the present invention is not limited this, and can be similarly applied to a case where image data are collected by another medical imaging apparatus, such as a magnetic resonance imaging apparatus, by using a contrast medium.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical imaging apparatus comprising:
an imaging-data collecting unit that collects imaging data by imaging a subject to whom a contrast medium is injected;
a first image creating unit that creates a first image on which an artery blood flow is highlighted, based on imaging data in an artery phase from which artery blood-flow dynamic states can be observed;
a second image creating unit that creates a second image on which a tumor is highlighted, based on imaging data in a late phase which is a time phase that appears after the artery phase from which presence of a tumor can be determined;
an image compositing unit that creates a third image by combining the first image and the second image; and
an image display unit that displays the third image composited by the image compositing unit;
wherein the image compositing unit composites an image such that display of the first image changes in accordance with information on the second image, when compositing the third image; and
wherein the image compositing unit composites an image such that display color of the first image changes in accordance with information on the second image.

2. The apparatus according to claim 1, wherein the first image and the second image are any one of two-dimensional images and three-dimensional images.

3. The apparatus according to claim 1, wherein the image compositing unit composites an image such that display of the first image changes in accordance with a voxel value in the second image, when the first image and the second image are three-dimensional images.

4. The apparatus according to claim 1, wherein the image compositing unit extracts a contour of a tumor on the second image, and composites an image such that display of the first image changes in accordance with positional relation to the contour.

5. A medical image processing apparatus comprising:
an imaging-data acquiring unit that acquires imaging data obtained by imaging a subject to whom a contrast medium is injected;
a first image creating unit that creates a first image on which an artery blood flow is highlighted, based on imaging data in an artery phase from which artery blood-flow dynamic states can be observed;
a second image creating unit that creates a second image on which a tumor is highlighted, based on imaging data in a late phase which is a time phase that appears after the artery phase and from which presence of a tumor can be determined;
an image compositing unit that creates a third image by combining the first image and the second image; and
an image display unit that displays the third image composited by the image compositing unit;
wherein the image compositing unit composites said third image such that display of the first image changes in accordance with information on the second image, when compositing the third image; and
wherein the image compositing unit composites an image such that display color of the first image changes in accordance with information on the second image.

6. A medical image processing method comprising:

acquiring imaging data obtained by imaging a subject to whom a contrast medium is injected;

creating a first image on which an artery blood flow is highlighted, based on imaging data in an artery phase from which artery blood-flow dynamic states can be observed;

creating a second image on which a tumor is highlighted, based on imaging data in a late phase which is a time phase that appears after the artery phase and from which presence of a tumor can be determined;

creating a third image by combining the first image and the second image, comprising, in the third image, changing the display color of the first image in accordance with information in the second image; and displaying the third image.

* * * * *